United States Patent [19]

Utsugi

[11] 4,408,612
[45] Oct. 11, 1983

[54] ULTRASONIC SCANNING DEVICE FOR EXAMINING VISCERA

[75] Inventor: Mikio Utsugi, Machida, Japan

[73] Assignee: Olympus Optical Co., Ltd., Tokyo, Japan

[21] Appl. No.: 245,100

[22] Filed: Mar. 18, 1981

[30] Foreign Application Priority Data

Mar. 29, 1980 [JP] Japan .................................. 55-40688

[51] Int. Cl.$^3$ ............................................. A61B 10/00
[52] U.S. Cl. ..................................................... 128/660
[58] Field of Search ................................ 128/660–663, 128/4, 6–8; 73/623

[56] References Cited

U.S. PATENT DOCUMENTS

| 3,779,234 | 12/1973 | Eggleton et al. | 128/660 |
| 4,008,603 | 2/1977 | Paulissen | 73/623 |
| 4,274,421 | 6/1981 | Dory | 128/660 |

FOREIGN PATENT DOCUMENTS

| 95285 | 2/1963 | Denmark | 128/6 |
| 2424733 | 1/1980 | France | 128/663 |
| 54-1984 | 1/1979 | Japan | 128/660 |
| 54-1460 | 9/1979 | Japan | 128/660 |

OTHER PUBLICATIONS

Hisanaga et al., "A Transesophageal ... Scanner ... ", Proc. 23rd Ann. Meeting of the AIUM, 1978, p. 47.
Hisanaga et al., "A New Trans-Digestive-Tract Scanner ... ", Proc. 23rd Ann. Meeting of the AIUM, 1978, p. 108.
Taylor et al., "A High-Resolution ... System", Ultrasound in Med. & Bio., vol. 5, No. 2, pp. 129–138, 1979.

Primary Examiner—Lee S. Cohen
Attorney, Agent, or Firm—Frishauf, Holtz, Goodman & Woodward

[57] ABSTRACT

An ultrasonic scanning device for examination of viscera comprises a control section containing an electric motor for scanning by ultrasonic beams, a flexible insertion section connected to the control section, a chamber provided in the distal end portion of the insertion section, a scanning mechanism provided in the chamber to scan a viscus by ultrasonic beams sent forth from an ultrasonic vibrator, an axially extending hole which is formed in the insertion section for communication with the chamber and into which a flexible rotation torque-transmitting linear member is inserted to connect the motor to the scanning mechanism, a seal member for tightly liquid sealing the lateral wall of the control section, and a liquid filled in the chamber and axially extending hole. The application of the linear member has the advantage of enabling the insertion section to be reduced in outer diameter, rendered flexible and easily inserted into a coeliac cavity. Further, the flow of the liquid from the chamber to the axially extending hole reduces the rotation torque of the scanning mechanism.

7 Claims, 4 Drawing Figures

ULTRASONIC SCANNING DEVICE FOR EXAMINING VISCERA

BACKGROUND OF THE INVENTION

This invention relates to an ultrasonic scanning device, which, when inserted into a tubular coeliac cavity, examines the viscera disposed around the tubular coeliac cavity by ultrasonic scanning.

An ultrasonic scanning device for examining viscera which is provided with a flexible insertion section is generally classified into the type which carries out scanning electronically and the type which performs scanning mechanically.

The distal end portion of the insertion section of the electronic scanner contains an ultrasonic transmission-reception unit. Therefore, the insertion section is rendered too thick to be smoothly introduced into the tubular coeliac cavity.

The distal end portion of the insertion section of the ordinary mechanical scanner contains a vibrator. This vibrator rotates about the central line of the distal end portion by a proper means.

One of the known ultrasonic scanning devices contains an electric motor and an angle detector in its distal end portion, resulting in a bulky construction.

The use of a pulse motor whose driving pulse signals are changed to motor angle information eliminates the angle detector. But, the distal end portion of the mechanical scanner which contains the pulse motor is unavoidably rendered too thick for easy insertion into a tubular coeliac cavity. Moreover, such a small pulse motor as is contained within the distal end portion is driven at as broad an angle as 60° per pulse. Therefore, an image of a viscus to be examined which appears on a display device is extremely rough, probably failing to assure the correct examination of the viscus. If a gear mechanism is applied to cause the vibrator to be rotated at a smaller angle per drive pulse of the pulse motor, it is indeed possible to obtain a distinct image of a viscus. However, the vibrator is rotated at a slower speed, not only consuming much time in the examination of the viscus, but also resulting in the failure to accurately examine a viscus whose physiological condition varies with time.

The distal end portion of the insertion section of another mechanical scanner comprises a vibrator which is unrotatable relative to the distal end portion, and a reflector for reflecting in prescribed directions ultrasonic waves delivered from the vibrator as those supplied thereto. With this type of mechanical scanner, the reflector is rotated by the control section with the aid of a linear member extending through the insertion section. With this mechanical scanner, the stationary vibrator is disposed in the distal end portion nearer to the control section than the reflector. Therefore, the reflector-rotating linear member cannot be fixed to the center of the reflector, but the linear member is fitted to the peripheral edge of the reflector, making it necessary to let the reflector rotate about the vibrator. Now let it be assumed that the insertion section of the scanner is flexible. Under this condition, the linear member should also be flexible. When the linear member is let to revolve around the axis in an extended state by the control section to effect the rotation of the reflector, then said linear member tends to be undesirably deformed into a helical shape. As a result, the movement of the reflector does not exactly follow the rotation angle of the linear member at the control section, probably leading to failure to obtain a correct image of a viscus and, consequently, failure to carry out its reliable examination. With the second known type of scanner, it is substantially impossible to apply a flexible insertion section.

With any of the conventional ultrasonic scanners, the reflector is surrounded with air in the distal end portion, resulting in a decline in the propagation rate of ultrasonic waves through the distal end portion and the corresponding decrease in the precision of examination.

It is accordingly the object of this invention to provide an ultrasonic scanner for examination of viscera, wherein the reflector is always rotated at a prescribed speed in spite of the narrow construction of a distal end portion; ultrasonic waves propagate smoothly between an ultrasonic wave transmission-reception unit and the inner wall of a coeliac cavity, thereby assuring the display of a reliable viscus image and consequently the high precision examination of the viscus.

SUMMARY OF THE INVENTION

To attain the above-mentioned object, this invention provides an ultrasonic scanner for viscera which comprises a control section having two ends, an elongate flexible insertion section which has two ends, one end being fixed to one end of the control section, a distal end portion which is formed in the other end of the insertion section, has a peripheral wall, and contains a chamber which is open at the peripheral wall and has front and rear end faces, an ultrasonic wave transmission-reception unit provided on the front end face of the chamber, an ultrasonic wave reflector which has two ends, one end being rotatably set adjacent to the rear end face the chamber, and the other end being provided with an inclined reflection plane facing the opening of the distal end portion and ultrasonic signal transmission-reception unit at predetermined angles, a reflector-driving motor provided in the control section, a flexible linear member which extends through the insertion section, has two ends, one end being fixed to the reflector-driving motor and the other end being fixed to said one end of the ultrasonic wave reflector, and transmits the rotation of the reflector-driving motor to the ultrasonic wave reflector, a flexible guide tube extending through the insertion section and having two ends, one end being connected to the control section and the other end being connected to the distal end portion, said flexible guide tube containing the flexible linear member extending therethrough, and an ultrasonic wave propagating liquid filled in the chamber.

A relatively large reflector-driving motor is received in the control section. A fine flexible linear member is used to transmit the rotation of the reflector-driving motor to the ultrasonic wave reflector. Therefore, the insertion section can be rendered narrow and flexible for easy insertion particularly into a tubular coeliac cavity which is bent or meanders. Further with an ultrasonic scanning device embodying this invention, a liquid concurrently acting as a medium for propagating ultrasonic waves and also as a lubricant is filled in the chamber to lubricate the inner wall of the axially extending hole of the distal end portion. Provision of the liquid not only assures the reliable propagation of ultrasonic waves through the chamber but also minimizes the rotation torque of the ultrasonic wave reflector. Therefore, the narrow flexible linear member can be applied as means for transmitting the rotation of the reflector-driving motor to the ultrasonic wave reflector. The linear member extending through a flexible guide tube passing through the insertion section is protected from the other portions of the insertion section. The loose insertion of the linear member into the flexible guiding tube and the lubricating action of a liquid filled in the flexible guide tube enables the rotation of the reflector-driving motor to be accurately transmitted to the ultrasonic wave reflector with a small rotation torque without accompanying the twist of the linear member even if it is bent or meanders.

This invention will be detailed with reference to the accompanying drawings.

DETAILED DESCRIPTION

Figure 1:
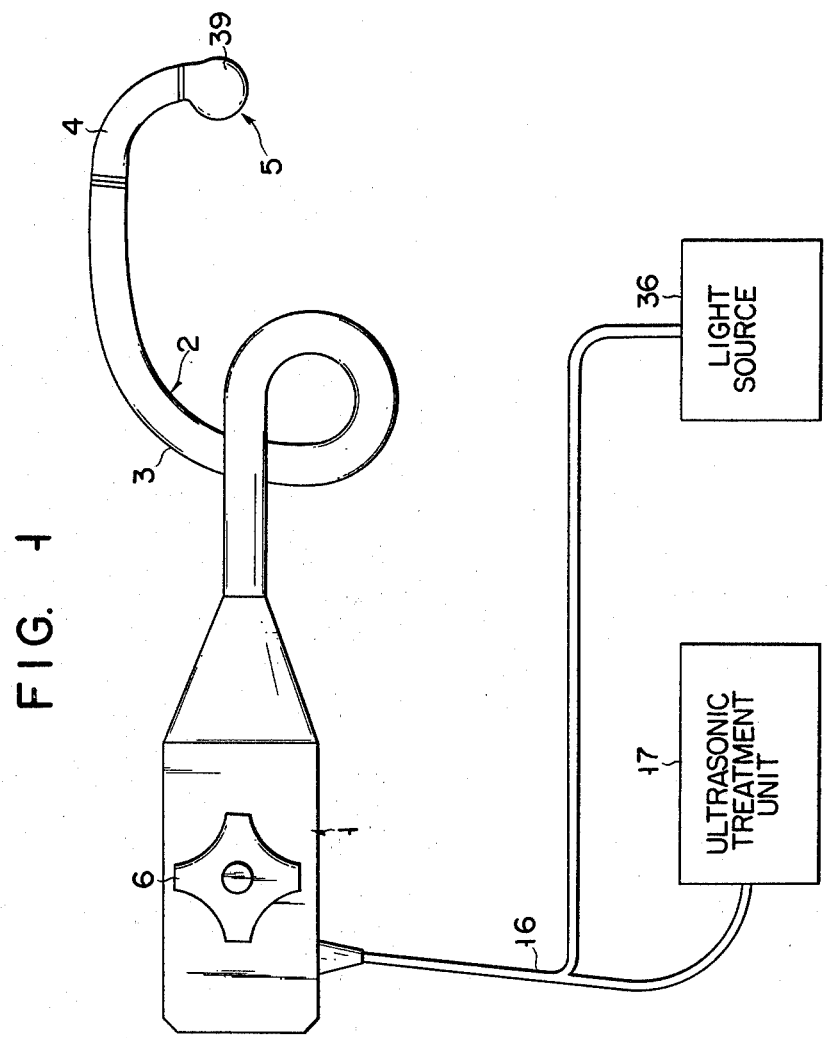
FIG. 1 is a plan view of an ultrasonic scanner embodying this invention for examination of viscera.

Referring to FIG. 1, an ultrasonic scanner embodying this invention for examination of viscera (hereinafter simply referred to as "the scanner") comprises a substantially parallelepiped control section 1 and a cylindrical flexible insertion section 2 extending from one end of the control section 1. The insertion section 2 comprises a flexible tube portion 3 constituting the greater part of the insertion section 2, a bend portion 4 fixed at one end to the forward end of the flexible tube portion 3 and a distal end portion 5 whose rear end is fixed to the other end of the bend portion 4.

The flexible tube portion 3 and bend portion 4 are constructed in the same manner as those of the ordinary endoscope, description thereof being omitted. Wires fixed at one end to the rear end of the distal end portion 5 extend through the insertion section 2. The wires are engaged at the other end with a control knob 6 provided at the control section 1. When the control knob 6 is rotated, the wires are pushed or pulled. As a result, the bend portion 4 is flexed, to set the distal end portion 5 in a desired direction. However, the wires and the mechanism for their operation are already known, illustration and description thereof being omitted.

Figure 3:
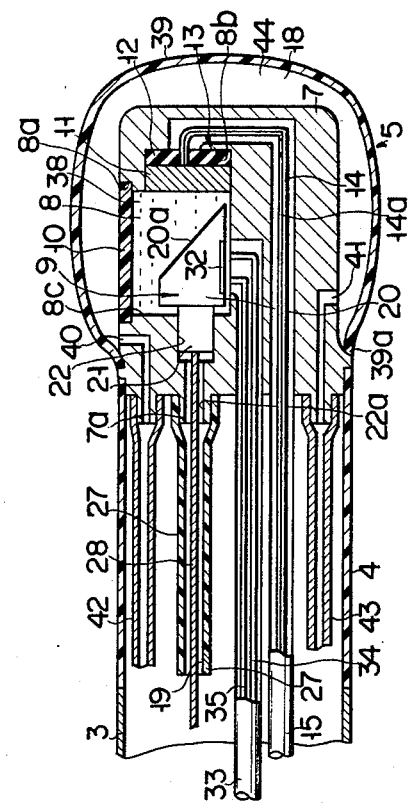
FIG. 3 is a longitudinal sectional view of the distal end portion of the scanner of FIG. 1.

As shown in FIG. 3, the distal end portion 5 comprises a cylindrical body 7 formed of metal such as stainless steel. The rear end of the cylindrical body 7 is fixed to the other end of the bend portion 4. Provided in the cylindrical body 7 is a substantially parallelepiped chamber 8 open at the peripheral wall of the cylindrical body 7. The later described ultrasonic beam scanning mechanism 9 is set in the chamber 8.

The opening 8a of the chamber 8 is closed in a liquid-tight state by a substantially rectangular window 10 made of a transparent synthetic resin such as polyethylene.

Fitted to the inner end face 8b of the chamber 8 which faces the distal end of the cylindrical body 7 is a disc-shaped vibrator 11 (made of, for example, piezoelectric material such as barium titanate and lead zirconate). This vibrator 11 transmits and receives ultrasonic waves by an ultrasonic wave damper 12 made of vibration-absorbing material such as (iron powder contained rubber). The ultrasonic wave damper 12 and vibrator 11 jointly constitute an ultrasonic wave transmission-reception unit 13.

A pair of signal leads 14, 14a inserted into a tube 15 extend through the insertion section 2. The signal leads 14, 14a are for the emission of ultrasonic waves and for the reception of ultrasonic wave echoes. The signal leads 14, 14a are connected to the corresponding ends of two extension leads passing through an extension cord 16 (FIG. 1) which extends from the housing of the control section 1. The other end of the extension cord 16 is connected to the later described ultrasonic treatment unit 17 (FIG. 1). Pulse signals from the ultrasonic treatment unit 17 and electric signals converted from echo signals by the vibrator 11 are transmitted through the signal leads 14, 14a and the extension leads in a time division fashion.

The ultrasonic beam scanning mechanism 9 comprises a solid cylindrical ultrasonic wave reflector 20 made of, for example, stainless drive shaft 21 concentrically fitted to the rear end of the reflector 20. The forward end face of the reflector 20 is formed into a reflection plane 20a inclined to the axis at an angle of 45°. An axially extending hole 22 open to the chamber 8 is formed at that part of the distal end portion which faces the rear end of the cylindrical body 7, that is, at the rear end face 8c of the chamber 8. The shaft 21 of the reflector 20 is rotatably fitted into the hole 22. The reflector 20 is concentrically disposed with the vibrator 11 and is rotatable about its own axis.

The shaft 24 (FIG. 2) of a reflector-driving motor 23 such as a DC motor which is set in the control section 1 is inserted into an axially extending hole 25 formed in the distal end portion of the control section 1. A seal member 26 such as an O-ring is inserted between the drive shaft 24 and the inner wall of the axially extending hole 25 to seal the intervening space.

A flange 1a is formed on the front end face of the control section 1. The interior space of the flange 1a defines part of the axially extending hole 25. A flange 7a (FIG. 3) is formed on the rear end face of the cylindrical body 7 of the distal end portion 5. The interior space of the flange 7a defines part of a smaller diameter hole 22a concentrically formed with the axially extending hole 22. A flexible guide tube 27 extends through the flexible tube portion 3. The ends of the flexible guide tube 27 corresponding to the flanges 1a, 7a are securely surrounded thereby.

An elongate flexible rotation torque-transmitting member (or linear member) 28 is inserted into the flexible guide tube 27 and extends out of the end of guide tube 27 and into the axially extending hole 22. This rotation torque-transmitting member 28 is formed of, for example, twisted steel wire strands with a smaller diameter than the inner diameter of the flexible guide tube 27. Concentrically fixed to the forward end of the shaft 24 of the reflector-driving motor 23 and the rear end of the shaft 21 of the reflector 20 are the corresponding ends of the rotation torque-transmitting member 28. The rotation torque-transmitting member 28 may comprise an elongated coil formed by closely winding a metal wire such as a steel wire.

The inner wall 19 of an axially extending guide tube 27 (FIG. 3) is formed of a material having a small friction coefficient such as tetrafluoroethylene or a copolymer of tetrafluoroethylene and hexafluoropropylene.

A gap of, for example, about 0.05 mm is provided between the inner wall 19 of the axially extending guide tube 27 and linear rotation torque-transmission member 28 to assure the free rotation of the rotation torque-transmitting member 28 and the prevention of its meandering. Namely, the member 28 has an outer diameter about 0.1 mm smaller than the inner diameter of the flexible guide tube 27.

The flexible guide tube 27 is covered with a metal net tube made of, for example, stainless steel in order to assure mechanical strength. The flexible guide tube 27 prevents the linear rotation torque-transmitting member 28 from being obstructed in operation due to the contact or entanglement of the member 28 with other elements of the flexible tube portion 3.

A motor rotation angle detector 29 such as a shaft encoder is provided in parallel with the reflector-driving motor 23 in the control section 1. The detector 29 detects the rotation angle of the shaft of the reflector-driving motor 23, namely, the rotation angle of the reflector 20 and controls the rotation speed. The rotation of the reflector-driving motor 23 is transmitted to the detector 29 by means of the shaft 24 of the motor 23 and gears 30, 31 fixed to the shaft 29a of the detector 29. The detector 29 converts the rotation angle of the motor 23 to an electric signal and transmits it to the later described echo display device 49.

Referring to FIG. 3, an elongate light reflection mirror 32 having an arc shape in cross section (the arc extending, for example, at central angle of 80° with the axis of the mirror 32 as its center) is provided on that side of the reflector 20 which is opposite to that on which the inclined reflection plane 20a is formed.

A pair of optical fibers 34, 35 pass through a flexible tube 33 extending through the control section 1 and insertion section 2. The optical fiber 34 passes through the extension cord 16. One end face of the optical fiber 34 is flush with the bottom plane of the chamber 8, and faces the lateral wall of the ultrasonic wave reflector 20 in the rotation region of the light-reflecting mirror 32. The other end of the optical fiber 34 is optically connected to a light source 36 (FIG. 1).

One end face of the other optical fiber 35 is flush with the bottom plane of the chamber 8 and set tandem with said one end face of the aforesaid optical fiber 34 along the shaft of the ultrasonic wave reflector 20, faces the lateral wall of the reflector 20 in the rotation region of the light-reflecting mirror 32. The other end of the optical fiber 35 is optically connected to the later described photoelectric conversion element 37 such as an epitaxial type silicon phototransistor which is provided in the control section 1.

The chamber 8 is filled with a liquid 38. The liquid 38 is also present between the axially extending hole 22 and the drive shaft 21 of the ultrasonic wave reflector 20, and further pervades the axially extending hole 19. The liquid 38 acts as a medium for the propagation of ultrasonic waves in the chamber 8 and plays the part of a lubricant in the axially extending hole 22 to minimize friction between the hole 22 and the drive shaft 21 as well as between the inner wall of the flexible guide tube 27 and the outer peripheral wall of the linear rotation torque-transmitting member 28. The liquid 38 is prepared from, for example, silicone oil or water without air.

The whole of the cylindrical member 7 of the distal end portion 5 is enclosed in a bag 39 made of an elastic material such as natural rubber or silicone rubber. The edge 39a of the bag 39 is fixed to the base of the cylindrical body 7 to render the interior of the bag 39 liquid-tight with respect to the outside. The cylindrical body 7 is provided with a liquid-introducing path 40 and liquid-discharging path 41. These paths 40, 41 are open to the interior of the bag 39 at the rear end of the lateral wall of the cylindrical body 7. These liquid-conducting paths 40, 41 are respectively connected to the corresponding ends of a flexible liquid inlet tube 42 and liquid outlet tube 43 both extending through the insertion section 2 of the endoscope. The liquid-conducting paths 42, 43 extend through the control section 1 and also inlet and outlet ports (not shown) provided above the housing of the control section 1, and are respectively connected to a liquid supply device and liquid suction device (neither shown). A liquid handled by both devices well serves the purpose, if it is not mixed with gas preventing the propagation of ultrasonic waves and is not subject to chemical changes. Most preferred is running water which is inexpensive and can be thrown away liberally.

When a liquid 18 is conducted through the tube 42 and liquid-introducing path 40 by the liquid supply device, the liquid 18 is brought into a space 44 defined between the bag 39 and the outer peripheral wall of the cylindrical body 7 to expand mainly the bag 39 radially of the cylindrical body 7. Conversely, when the liquid-discharging device is actuated, the liquid 18 held in the space 44 is drawn off, causing the bag 39 to be contracted.

Figure 4:
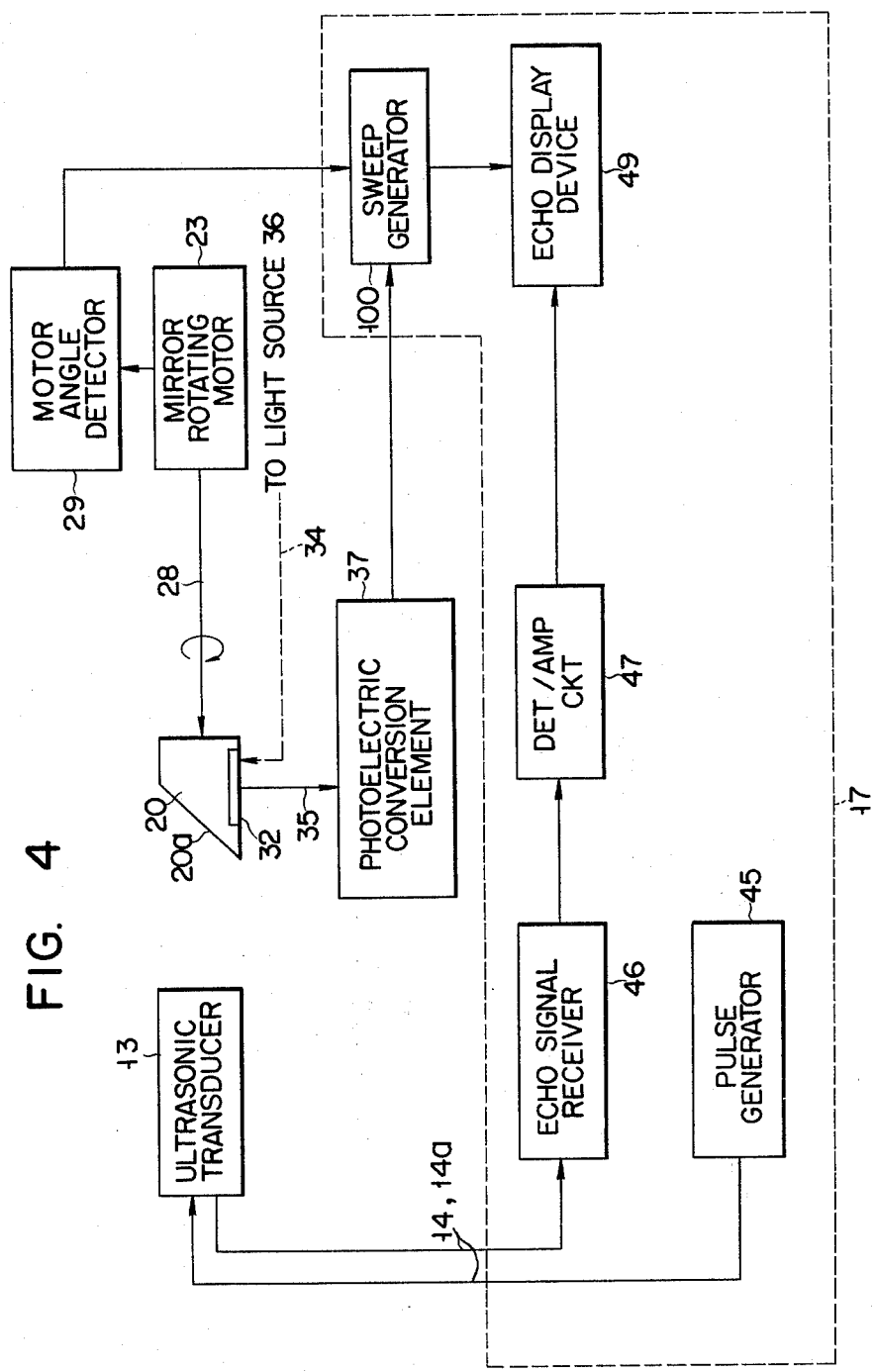
FIG. 4 is a block circuit diagram of the scanner of FIG. 1.

Referring to FIG. 4, an ultrasonic treatment unit 17 comprises a pulse generator 45 for sending a pulse signal to the vibrator 11 of the ultrasonic wave transducer (ultrasonic transducer) 13 through signal leads 14, 14a. The ultrasonic treatment unit 17 further comprises an echo signal receiver 46 for receiving output echo signals from the vibrator 11 of the ultrasonic wave transceiver 13 through the signal leads 14, 14a, and a detector/amplifier circuit 47 and echo display device 49 containing, for example, a cathode-ray tube, the last two elements being connected to the echo signal receiver 46 in the order mentioned.

An output signal is supplied from the photoelectric conversion element 37 to a sweep-generator 100 connected thereto. When both the output signal from the element 37 and an electric pulse from the rotation angle detector 29 are supplied to the generator 100, it allows a bright spot to draw a scanning line in a required position on the cathode-ray tube of the echo display device 49 at a required timing.

Figure 2:
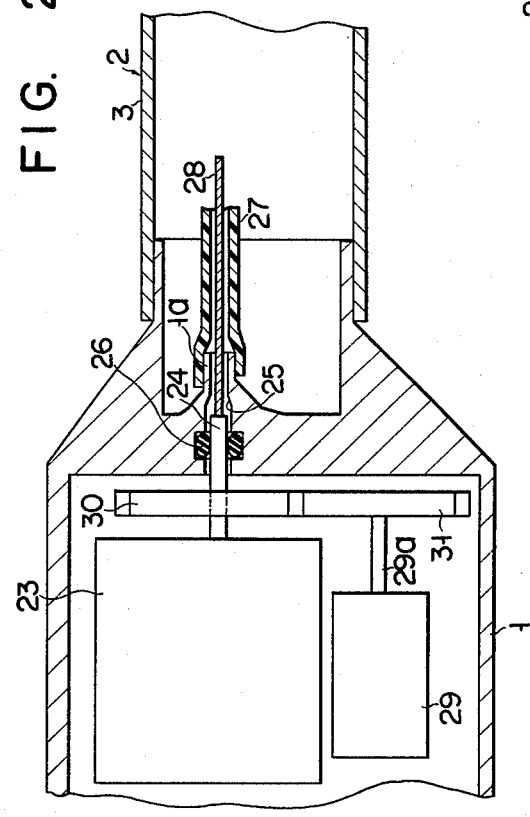
FIG. 2 is a longitudinal sectional view of the control section of the scanner of FIG. 1.

Description is now given with reference to FIGS. 2, 3 and 4 of the operation of the ultrasonic scanning device embodying this invention. In this case, the stomach, for example, is taken as a viscus to be examined by ultrasonic waves. Obviously, the ultrasonic scanning device of the invention can examine any other coeliac cavity than the stomach.

First, the liquid 18 is drawn off from the bag 39 to contract it. The insertion section 2 of the scanning device is inserted into the stomach to the desired depth. The opening 8a of the chamber 8 is directed toward a viscus to be examined, and drawn near thereto. The liquid 18 is filled in the space 44 of the bag 39 to swell it. As a result, the bag 39 is pressed against the inner wall of the stomach. The reflector-driving motor 23 is actuated. While the ultrasonic wave reflector 20 is rotated by means of the linear rotation torque-transmitting member 28, electric pulses are sent forth from the pulse generator 45 to the vibrator 11 of the ultrasonic wave transceiver 13 through the signal leads 14, 14a. The pulses are converted into ultrasonic waves by the vibrator 11. The converted ultrasonic waves are emitted to the ultrasonic wave reflector 20 in its axial direction, and reflected at right angles by the inclined reflection plane 20a. When the reflection plane 20a faces the opening 8a of the chamber 8, reflected ultrasonic waves are sent forth from the distal end portion through the opening 8a and pass through the tissue of a specimen to a viscus to be examined. Echoes from the viscus enter the opening 8a, and are reflected by the reflection plane 20a to be brought to the vibrator 11. The reflected echoes are converted into electric pulses by the vibrator 11. The converted electric pulses are caught by the echo signal receiver 46 through the signal leads 14, 14a, and amplified by the detector/amplifier circuit 47 and then conducted to the echo display device 49. As previously described, the chamber 8 and bag 39 are filled with a liquid 18 for propagating ultrasonic waves, thereby assuring the reliable transmission of ultrasonic waves between the vibrator 11 and viscus.

When an ultrasonic scanning plane is to be indicated on the echo display device 49, it is necessary to obtain further information showing accurately that point on the echo display device 49 at which echo signals generated in the successive moments are to be displayed in addition to the aforesaid echo signals. In this case, the light-reflecting mirror 32, rotation angle detector 29, and sweep-generator 100 jointly play the part of supplying the echo display device 49 with information on the position in which the above-mentioned momentarily-generated echo signals are to be displayed.

The rotation angle detector 29 coupled to the mirror-rotating motor 23 is rotated through a prescribed angle, when the mirror-rotating motor 23 is driven through a predetermined angle. When an electric pulse is issued for each prescribed rotation of the rotation angle detector 29, the sweep-generator 100 causes scanning lines corresponding to the shifting of a bright spot to be indicated one after another on the display device 49, each time the electric pulse is received. A space interval between these scanning lines is predetermined on the display device 49.

It is only when an output light from the light source 36 is brought into the photoelectric conversion element 37 by means of the light-reflecting mirror 32 and optical fibers 34, 35, that the sweep-generator 100 receives a photoelectrically converted electric signal. It is during this period only that the sweep-generator 100 causes a scanning line to be drawn on the echo display device 49 upon receipt of the aforesaid electric pulse signal. Therefore, scanning lines are drawn only within a certain area of the echo display device 49.

In each cycle, a scanning line is always drawn by the bright spot on the echo display device 49 immediately after an electric signal is supplied from the photoelectric conversion element 37. A scanning line drawn at the spot defines a boundary on one side of the display area of the echo display device 49.

Description is now given of the relationship between the area of the echo display device 49 where a scanning line is drawn and the construction of the scanner.

A light is irradiated on the peripheral wall of the ultrasonic wave reflector 20 from the light source 36 through the optical fiber 34. The light-reflecting mirror 32 has a smaller width than that which corresponds to an angle defined by two edges extending axially of the opening 8a of the chamber 8 with the axis of the ultrasonic wave reflector 20 taken as the center. Therefore, it is only when echoes can enter the chamber 8 at its opening 8a, that the light-reflecting mirror 32 reflects a light on the end face of the optical fiber 34 opposite to the chamber 8. The reflected light is irradiated on the end face of the other optical fiber 35 opposite to the chamber 8. In cases other than described above, the end face of the optical fiber 34 does not face the light-reflecting mirror 32. Consequently, a light sent forth from the end face is not irradiated on the end face of the other optical fiber 35.

It is only when an echo ultrasonic wave enters the chamber 8 at its opening 8a, that the light-reflecting mirror 32 of the echo display device 49 causes a light signal to enter the photoelectric conversion element 37. A scanning line begins to be drawn from this moment at a point corresponding to the rotation angle of the mirror-rotating motor 23.

A detected and amplified echo signal delivered to the echo display device 49 acts to change the luminosity of the bright spot.

The foregoing description refers to the mechanism by which an ultrasonic scanning plane is drawn in accordance with the intensity of momentarily supplied echo signals.

As previously described, a timing in which a scanning line is drawn in a certain area of the echo display device 49 is defined by the rotation angle of the mirror-rotating motor 23. More correctly, said timing should be determined by the rotated position of the ultrasonic wave mirror 20. When a discrepancy arises between the rotated position of the mirror-rotating motor 23 and that of the ultrasonic wave mirror 20, a position on the echo display device 49 in which a scanning line is to be drawn is displaced from an ideal point. The present invention is intended to assure accurate conformity between the rotated position of the mirror-rotating motor 23 and that of the ultrasonic wave mirror 20. Since the ultrasonic reflector 20 is rotated about its axis, the ultrasonic scanning plane becomes perpendicular to the axis and the images of the section of the examined viscus on the plane are indicated on the echo display device 49 in succession.

It is further possible to let the ultrasonic scanning device concurrently act as an endoscope by setting a lateral view type objective in the cylindrical body 7 of the distal end portion 5 in a state facing the bottom of the chamber 8; providing an eyepiece section at the proximal end of the control section 1; optically connecting the objective and eyepiece section by an observation optical fiber bundle extending through the insertion section 2 and control section 1; and applying a light-transmitting optical fiber bundle extending from the light source 36 or any other light source through the control section 1 and insertion section 2 to emit a light to the outside like ultrasonic waves from the opening 8a of the chamber 8. The above-mentioned arrangement assures the observation of a coeliac cavity into which the insertion section 2 is introduced and also the easy placement of the distal end portion 5 in the coeliac cavity.

What is claimed is:

1. An ultrasonic scanning device for examining viscera, comprising:
   a control section having two ends;
   an elongate flexible insertion section having an opening therethrough and two ends, one end being fixed to one of said two ends of said control section;
   a distal end portion which is formed at the other end of said insertion section, said distal end portion having a peripheral wall, and a chamber open at said peripheral wall and being provided with front and rear end faces;

ultrasonic wave transmission-reception means provided on said front end face of said chamber;

means provided in said control section for pulsing and receiving echo signals from said ultrasonic wave transmission-reception means;

an ultrasonic wave reflector having two ends, one end of said reflector being rotatably disposed adjacent to said rear end face of said chamber, and the other end of said reflector being fitted with an inclined reflection plane facing said opening of said chamber of said distal end portion and ultrasonic wave transmission-reception means at a predetermined angle;

a motor provided in said control section for driving said ultrasonic wave reflector;

a flexible linear member which extends through said insertion section and has two ends, one end of said flexible linear member being fixed to said motor, and the other end of said flexible linear member being fixed to said one end of said ultrasonic wave reflector, said linear flexible member being so arranged as to transmit the rotation of said motor to said ultrasonic wave reflector;

a flexible guide tube extending through said insertion section and having two ends, one end of said flexible guide tube being connected to said control section and the other end of said flexible guide tube being connected to said distal end portion, said flexible linear member extending through said flexible guide tube;

a sealing member provided only at said one end of the flexible linear member effecting a liquid-tight seal between the interior of said guide tube and said motor;

a liquid filled in said chamber and in that portion of said flexible guide tube which extends between said sealing member and said other end of said flexible linear member; and closing means coupled to said chamber to close said chamber in a liquid-tight state to retain said liquid in said chamber, said closing means being ultrasonically transparent.

2. The ultrasonic scanning device according to claim 1, wherein said flexible linear member is loosely surrounded by said flexible guide tube, the inner face of said flexible guide tube comprising a flexible lubricating material which extends through said insertion section.

3. The ultrasonic scanning device according to claim 1 or 2, wherein:

that side of said ultrasonic wave reflector which is opposite to the side on which said reflection plane is formed is provided with a longitudinally elongate light-reflecting mirror;

said control section comprises a photoelectric conversion element; and said insertion section comprises first light-transmitting means for irradiating a light on the lateral wall of said opposite side of said ultrasonic wave reflector, and second light-transmitting means for supplying said photoelectric conversion element with a light reflected by said light-reflecting mirror and delivered from said first light-transmitting means.

4. The ultrasonic scanning device according to claim 1 or 2, wherein said liquid filled in said chamber is an ultrasonic wave-propagating liquid.

5. An ultrasonic scanning device for examining viscera which comprises:

a control section having two ends;

an elongate flexible insertion section having two ends, one end of said insertion section being fixed to one of said two ends of said control section;

a distal end portion which is formed at the other end of said insertion section, said distal end portion having a peripheral wall, and a chamber open at said peripheral wall and being provided with front and rear end faces;

ultrasonic wave transmission-reception means provided on said front end face of said chamber;

means provided in said control section for pulsing and receiving echo signals from said ultrasonic wave transmission-reception means;

an ultrasonic wave reflector having two ends, one end of said reflector being rotatably disposed adjacent to said rear end face of said chamber, and the other end of said reflector being fitted with an inclined reflection plane facing said opening of said chamber of said distal end portion and ultrasonic wave transmission-reception means at a predetermined angle, that side of said ultrasonic wave reflector which is opposite to the side on which said reflection plane is formed being provided with a longitudinally elongate light-reflecting mirror;

a motor provided in said control section for driving said ultrasonic wave reflector;

a flexible linear member which extends through said insertion section and has two ends, one end of said flexible linear member being fixed to said motor, and the other end of said flexible linear member being fixed to said one end of said ultrasonic wave reflector, said flexible linear member being so arranged as to transmit the rotation of said motor to said ultrasonic wave reflector;

a flexible guide tube extending through said insertion section and having two ends, one end of said flexible guide tube being connected to said control section and the other end of said flexible guide tube being connected to said distal end portion, said flexible linear member extending through said flexible guide tube; and an ultrasonic wave-propagating liquid filled in said chamber;

said control section comprising a photoelectric conversion element;

said insertion section comprising first light-transmitting means for irradiating a light on the lateral wall of said opposite side of said ultrasonic wave reflector, and second light-transmitting means for supplying said photoelectric conversion element with a light reflected by said light-reflecting mirror and delivered from said first light-transmitting means; and closing means coupled to said chamber to close said chamber in a liqquid-tight state to retain said liquid in said chamber, said closing means being ultrasonically transparent.

6. The ultrasonic scanning device according to any one of claims 1, 2, or 5, wherein said linear member is formed of twisted metal wire strands.

7. The ultrasonic scanning device according to any one of claims 1, 2 or 5, wherein said linear member comprises an elongate coil formed by closely winding a metal wire.

* * * * *